(12) United States Patent
Zhang et al.

(10) Patent No.: US 7,288,942 B2
(45) Date of Patent: Oct. 30, 2007

(54) PLASMA POTENTIAL MEASURING METHOD AND APPARATUS, AND PLASMA POTENTIAL MEASURING PROBE

(75) Inventors: Xin Zhang, Tokyo (JP); Naoyuki Sato, c/o Ibaraki University, 12-1, Nakanarusawa 4-Chome, Hitachi-shi, Ibaraki (JP); Takashi Ikehata, Ibaraki (JP); Kazutoshi Ogino, Kanagawa (JP)

(73) Assignees: Naoyuki Sato, Hitachi-shi, Ibaraki (JP); Hitachi Cable, Ltd., Chiyoda-ku, Tokyo (JP)

( * ) Notice: Subject to any disclaimer, the term of this patent is extended or adjusted under 35 U.S.C. 154(b) by 19 days.

(21) Appl. No.: 10/953,113

(22) Filed: Sep. 30, 2004

(65) Prior Publication Data
US 2005/0083065 A1 Apr. 21, 2005

(30) Foreign Application Priority Data
Oct. 2, 2003 (JP) ............................. 2003-344720
Oct. 2, 2003 (JP) ............................. 2003-344721

(51) Int. Cl.
*G01N 27/62* (2006.01)
(52) U.S. Cl. .................................................. 324/464
(58) Field of Classification Search ................ 324/464; 118/723 I, 723 R; 315/111.31
See application file for complete search history.

(56) References Cited

U.S. PATENT DOCUMENTS

| | | | | |
|---|---|---|---|---|
| 5,031,125 A | * | 7/1991 | Shimizu et al. ............. | 702/130 |
| 5,339,039 A | * | 8/1994 | Carlile et al. ............... | 324/655 |
| 5,705,931 A | * | 1/1998 | Klick .......................... | 324/464 |
| 6,585,891 B1 | * | 7/2003 | Ohkawa ...................... | 210/222 |
| 6,653,852 B1 | * | 11/2003 | Benjamin .................... | 324/754 |
| 6,885,153 B2 | * | 4/2005 | Quon ..................... | 315/111.31 |
| 6,902,646 B2 | * | 6/2005 | Mahoney et al. ....... | 156/345.24 |
| 2002/0114123 A1 | * | 8/2002 | Nishio et al. ............... | 361/234 |
| 2003/0121609 A1 | * | 7/2003 | Ohmi et al. ........... | 156/345.47 |

OTHER PUBLICATIONS

Kanji Fujita, "Plasma Potential Measurement by Emissive Probe", Journal of Physics, Soc. of Japan, vol. 39, No. 5 (1984), pp. 366-369.

* cited by examiner

*Primary Examiner*—Walter Benson
*Assistant Examiner*—Timothy J Dole
(74) *Attorney, Agent, or Firm*—McGinn IP Law Group, PLLC (57) ABSTRACT

A plasma potential measuring method is conducted by: providing a measurement space surrounded by a radio-frequency electric field in plasma atmosphere; varying a floating potential at an electrode located in the measurement space by the ponderomotive effect acted only on electrons; and determining as a plasma potential a value of the floating potential at the time when an ion current flown into the electrode begins to lower.

20 Claims, 8 Drawing Sheets

PLASMA POTENTIAL MEASURING METHOD AND APPARATUS, AND PLASMA POTENTIAL MEASURING PROBE

The present application is based on Japanese patent application Nos. 2003-344720 and 2003-344721, the entire contents of which are incorporated herein by reference.

BACKGROUND OF THE INVENTION

1. Field of the Invention

The invention relates to a plasma potential measuring method and apparatus, and more particularly to a plasma potential measuring method and apparatus that allows reduction in error factor. The invention also relates to a plasma potential measuring probe, and more particularly to a plasma potential measuring probe that allows accurate measurement in ion current.

2. Description of the Related Art

The emissive probe method is known as a method that allows the measurement of plasma potential in plasma atmosphere without any analysis.

Figure 1:
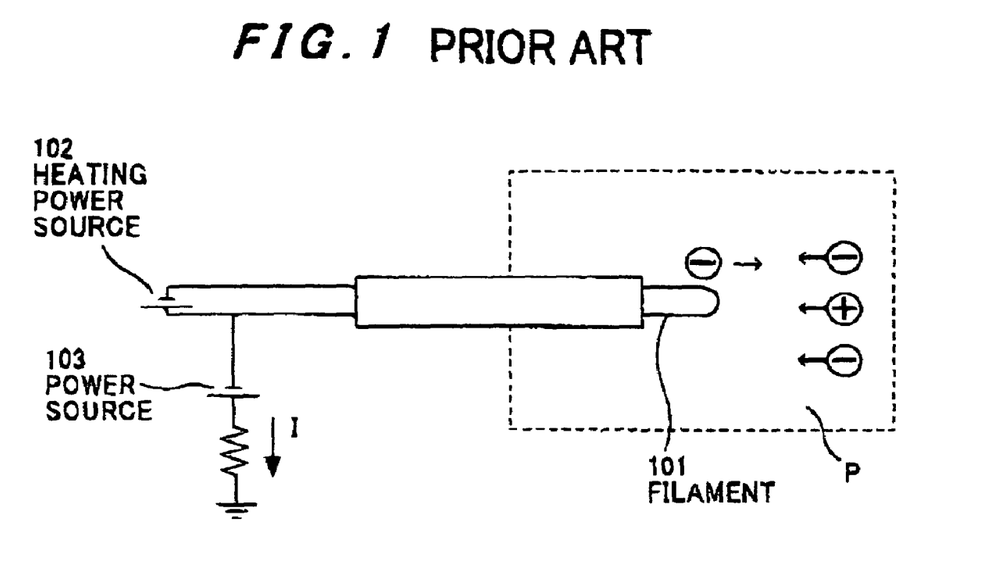
FIG. 1 is a system diagram showing a plasma potential measuring apparatus using the known emissive probe method.

FIG. 1 is a system diagram showing a plasma potential measuring apparatus using the known emissive probe method. As shown in FIG. 1, the emissive probe method is conducted such that a filament 101 in plasma atmosphere is heated by the application of current from a heating power source 102, a potential applied to the entire filament 101 is varied by a power source 103, and the plasma potential is determined to be a potential applied when no current I is flown into the filament 101 (i.e., in floating probe state) [for example, Kanji Fujita, "Plasma Potential Measurement by Emissive Probe", J. of Phys. Soc. of Jpn., vol. 39, No. 5(1984) 366-369].

The potential (floating potential) of floating probe without thermoelectronic emission is, as compared to plasma potential, reduced by a level (sheath voltage) corresponding to the energy of electron stream such that it satisfies the floating condition to block the electron stream from plasma. If thermoelectron is emitted from the floating probe, the stream of thermoelectron is in a direction to cancel the abovementioned electron stream and therefore, the sheath voltage lowers and the floating potential comes close to the plasma potential. If the floating potential exceeds the plasma potential, thermoelectron is not emitted.

However, the emissive probe method has some problems Namely, due to some error factors thereof, it is difficult to conduct the accurate measurement. Since the amount of thermoelectron generated varies depending on the temperature of filament 101, error in plasma potential measurement must be occurred depending on the filament temperature. Further, the filament 101 significantly wastes with time, and therefore the repeatability in measurement will deteriorate.

SUMMARY OF THE INVENTION

It is an object of the invention to provide a plasma potential measuring method that has a reduced error factor and a good repeatability in measurement.

It is a further object of the invention to provide a plasma potential measuring apparatus that has a reduced error factor and a good repeatability in measurement.

It is a further object of the invention to provide a plasma potential measuring probe that has a reduced error factor and a good repeatability in measurement.

According to one aspect of the invention, a plasma potential measuring method comprises the steps of:

providing a measurement space surrounded by a radio-frequency electric field in plasma atmosphere;

varying a floating potential at an electrode located in the measurement space; and determining as a plasma potential a value of the floating potential at the time when an ion current flown into the electrode begins to lower.

According to another aspect of the invention, a plasma potential measuring apparatus comprises:

an antenna that forms a measurement space surrounded by a radio-frequency electric field in a plasma atmosphere;

an electrode that is located in the measurement space;

an internal electrode that captures part of ions flown into the electrode;

an ion current determination section that determines a reduction in an ion current flown into the electrode; and a potential determination section that determines as a plasma potential a floating potential of the electrode at the time when the ion current begins to lower.

According to another aspect of the invention, a plasma potential measuring probe comprises:

one rod-shaped electrode that is used to apply radio-frequency power;

an opposite electrode that is used to apply radio-frequency power and is disposed by a gap distant from a front end of the one rod-shaped electrode;

a floating potential detecting electrode that is disposed in a radio-frequency electric field formed by radio-frequency power supplied to the one rod-shaped electrode and the opposite electrode; and an ion current detecting electrode that is disposed in the vicinity of the floating potential detecting electrode so as to capture part of an ion current flown into the floating potential detecting electrode.

BRIEF DESCRIPTION OF THE DRAWINGS

The preferred embodiments according to the invention will be explained below referring to the drawings, wherein.

DETAILED DESCRIPTION OF THE PREFERRED EMBODIMENTS

Figure 2:
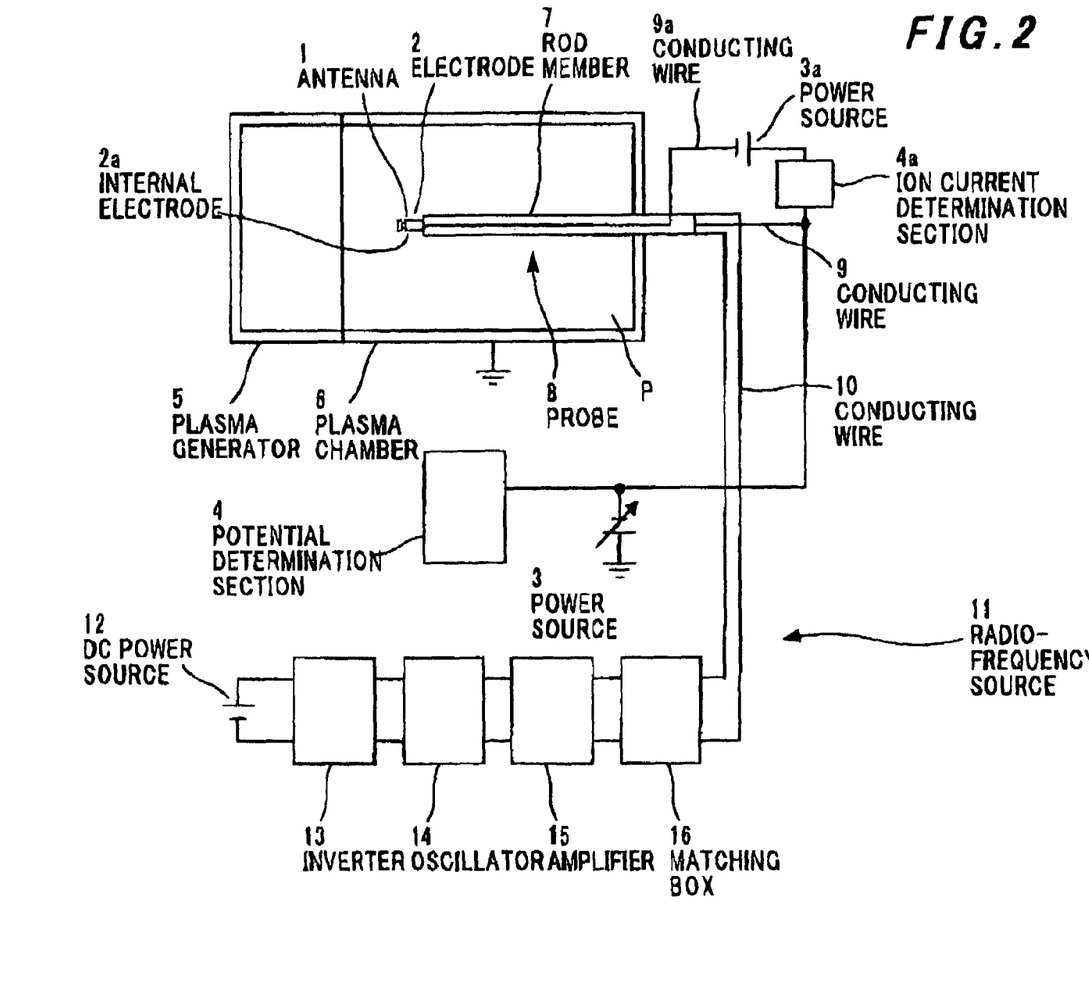
FIG. 2 is a system diagram showing a plasma potential measuring apparatus in a preferred embodiment according to the invention.

FIG. 2 is a system diagram showing a plasma potential measuring apparatus in the preferred embodiment according to the invention.

As shown in FIG. 2, the plasma potential measuring apparatus of the invention is composed of: an antenna 1 that forms a measurement space (See FIG. 5) surrounded by radio-frequency electric field E in plasma atmosphere P; an electrode 2 and an internal electrode 2a that are placed in the measurement space; a power source 3 that controls a potential applied to the electrode 2; a potential determination section 4 that determines as a plasma potential a potential applied when no current is flown into the electrode 2; and an ion current determination section 4a that determines reduction in ion current flown into the internal electrode 2a.

A plasma chamber 6 is connected to a plasma generator 5 to provide a plasma atmosphere. Thus, plasma generated by the plasma generator 5 is confined in the plasma chamber 6. It is estimated that plasma atmosphere P is, regardless of positions, in uniform plasma density and therefore in equal plasma potential. The chamber arrangement is for testing the plasma potential measuring apparatus of the embodiment. In practical use, the antenna 1 and electrode 2 can be used placed in plasma atmosphere in an arbitrary facility to be targeted.

The antenna 1 and electrode 2 are provided at the tip portion of a rod member 7 with a suitable length. The rod member 7, antenna 1 and electrode 2 compose the probe 8. Inside the probe 8, conducting wires for the antenna 1, electrode 2 and internal electrode 2a are laid passing through. Thus, by inserting the probe 8 into the plasma chamber 6 at one side thereof, the conducting wires are connected to outside of the plasma chamber 6.

The conducting wire 9 for the electrode 2 is connected to the power source 3 and to the potential determination section 4. The potential determination section 4 is allowed to detect a potential applied to the electrode 2 and a current flown from the power source 3 to the electrode 2. Therefore, it can read a potential applied at the moment when no current is flown while monitoring the change of current flow due to the control of the applied potential at the power source 3.

The electrode 2 has slits 21b (See FIG. 4) disposed in axial symmetry. A conducting wire 9a (See FIG. 4) for the internal electrode 2a disposed concentrically inside the electrode 2 is connected to the power source 3a (See FIG. 2) and to the ion current determination section 4a. The ion current determination section 4a is allowed to detect ion current flown from the power source 3a through the slits 21b to the electrode 2. The plasma potential is determined by a floating potential of the electrode 2 where the current of ion current determination section 4a begins to decrease in the process of increasing the radio-frequency electric field E, while monitoring both the floating potential of electrode 2 and the current at ion current determination section 4a.

On the other hand, two conducting wires 10 for the antenna 1 are connected to a radio-frequency source 11. The radio-frequency source 11 is composed of: a DC power source 12; an inverter 13 to switch the output of DC power source 12; an oscillator 14 to oscillate due to the switched power; an amplifier 15 to amplify the oscillation output of oscillator 14; and a matching box 16 to match an impedance from the amplifier 15 to the antenna 1. The radio-frequency source 11 is operable to supply radio-frequency power of GHz band to the antenna 1

Figure 3:
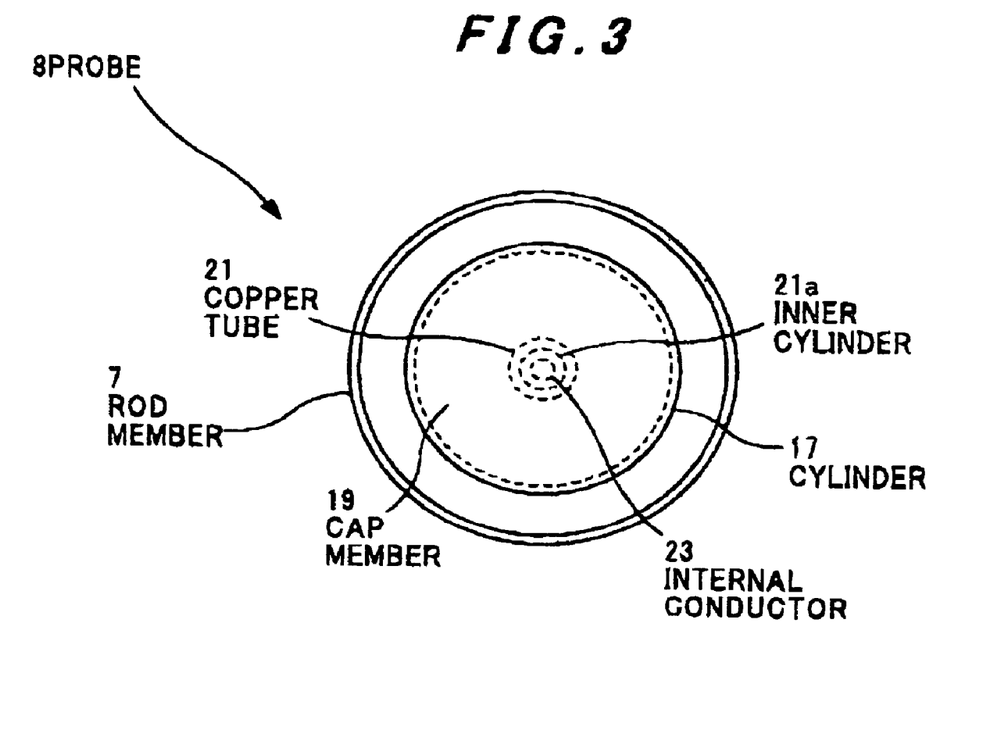
FIG. 3 is an end view showing a probe 8 of the plasma potential measuring apparatus in FIG. 2.

FIG. 3 is an end view showing the probe 8 of the plasma potential measuring apparatus in FIG. 2. As shown in FIG. 3, the probe 8 has a coaxial multiple structure. Namely, the outermost rod member 7 is a circular tube made of stainless steel (SUS304), and it allows the antenna 1 and electrode 2 to reach a plasma atmosphere in arbitrary facility while holding the entire probe 8 and it protects the members accommodated in the rod member 7. The rod member 7 may be made a glass tube whose inner wall is coated with high conductivity metal.

A cylinder 17 made of stainless steel (SUS304) and inserted into the rod member 7 is connected to one pole of conducting wire 10 (See FIG. 2) to serve as one electrode for radio-frequency application.

Figure 4:
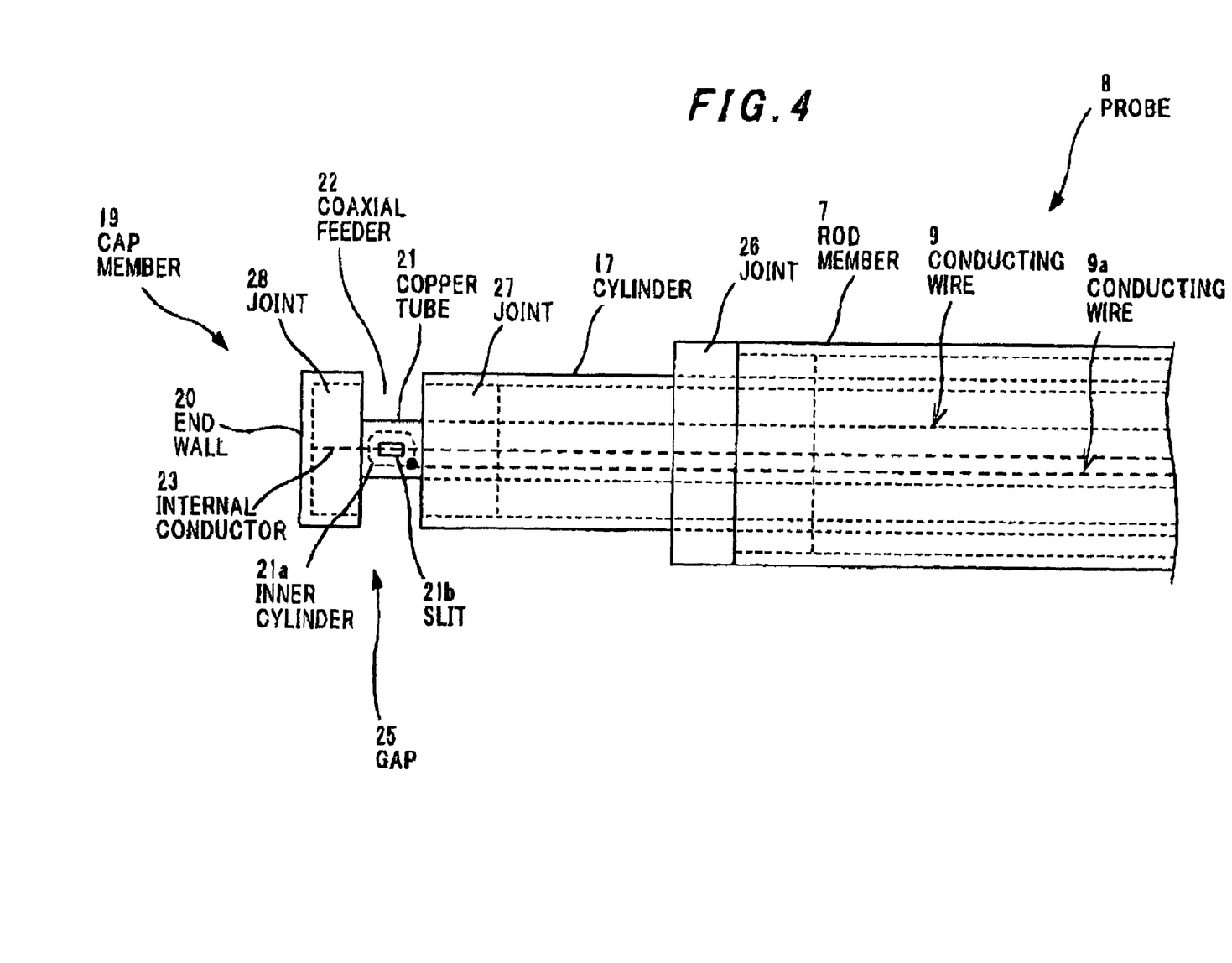
FIG. 4 is a side view showing the probe 8 of the plasma potential measuring apparatus in FIG. 2.

FIG. 4 is a side view showing the probe 8 of the plasma potential measuring apparatus in FIG. 2. The cylinder 17 is protruded from the front end of rod member 7 and is provided with a cap member 19 attached distant from its end. The cap member 19 is made such that a short cylinder of the same material as the cylinder 17 and with the same diameter as the cylinder 17 is at its end closed up using an end wall 20.

Inside the cylinder 17, a coaxial feeder 22 with a copper tube 21 as external conductor is disposed. The copper tuber 21 is connected to the conducting wire 9 (See FIG. 2). An internal conductor 23 of the coaxial feeder 22 is connected to the other pole of conducting wire 10 (See FIG. 2). The coaxial feeder 22 is further provided with a conductive inner cylinder 21a disposed between the external conductor, copper tube 21 and the internal conductor 23. The inner cylinder 21a (inner electrode) is connected to the conducting wire 9a (See FIG. 2) as shown in FIG. 4. The copper tube 21 protrudes from the front end of cylinder 17 and reaches the cap member 19. The internal conductor 23 is further ahead protruded and electrically connected to the end wall of cap member 19.

Radio-frequency power supplied from the radio-frequency source 11 to both poles of the conducting wires 10 is fed to the front end of cylinder 17 and the base end of cap member 19 that are opposed a gap 25 away from each other. Thus, the gap 25 composes the antenna 1. On the other hand, the copper tuber 21 exposed at the center of the gap 25 serves as the electrode 2 to generate a floating potential, and the inner cylinder 21a (inner electrode) serves as the electrode for ion current detection.

A joint 26 of synthetic resin (e.g., Teflon, a registered trademark) is provided at portion where the cylinder 17 is inserted into the rod member 7, thereby airtight-sealing the cylinder 17 while securing the coaxial feeder 22 at the center of cylinder 17. Further, a joint 28 of synthetic resin is provided at portion where the cap member 19 is attached to the coaxial feeder 22, thereby securing the cap member 19 at the center of coaxial feeder 22. The coaxial feeder 22 may be inserted into the joint 28.

The operation of the plasma potential measuring apparatus (FIG. 2) using the probe 8 (FIG. 4) will be explained below.

When radio-frequency power is supplied from the radio-frequency source 11 to both poles of conducting wires 10, the one pole is conducted through the inner face of cylinder 17 to the front end of cylinder 17, and the other pole is conducted from the internal conductor 23 through the inner face of cap member 19 to the base end of cap member 19.

Figure 5:
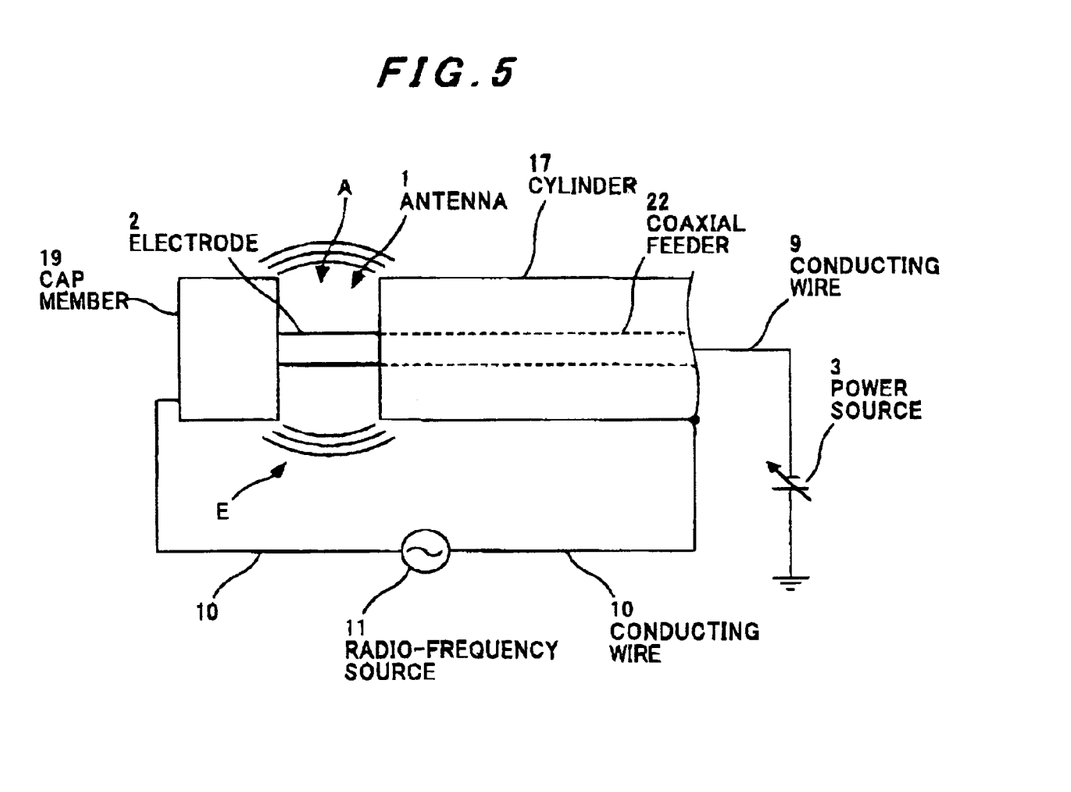
FIG. 5 is an explanatory diagram illustrating the operation of electrode and antenna composed according to the invention.

FIG. 5 is an explanatory diagram illustrating the operation of electrode and antenna composed according to the invention. However, in FIG. 5, the conducting wire 10 is illustrated such that it is directly connected from the radio-frequency source 11 to the cap member 19.

Thereby, as shown in FIG. 5, radio-frequency electric field E is generated at the antenna 1. Since the cylinder 17 and cap member 19 have a cylindrical structure with the same diameter, the radio-frequency electric field E is in axial symmetry (in rotational symmetry) generated all around the antenna 1. The radio-frequency electric field E allows that the measurement space A surrounded by the radio-frequency electric field E is formed by the effect of dynamic gravity (ponderomotive force) described later.

The potential from the power source 3 is applied to the copper tube 21 as external conductor of the coaxial feeder 22, and the copper tube 21 exposed at the center of the antenna 1 serves as the electrode 2. Thus, depending on the potential difference between the potential applied to the electrode 2 and the plasma potential, current flows from the electrode 2 into the plasma atmosphere or from the plasma atmosphere to the electrode 2. When the potential applied from the power source 3 is gradually adjusted from a low value to a high value, the change of current is monitored. The applied potential at the time when the current flow stops is read, and its potential value is determined as the floating potential.

The principle of plasma potential determination in the above operation will be explained below.

Figure 6:
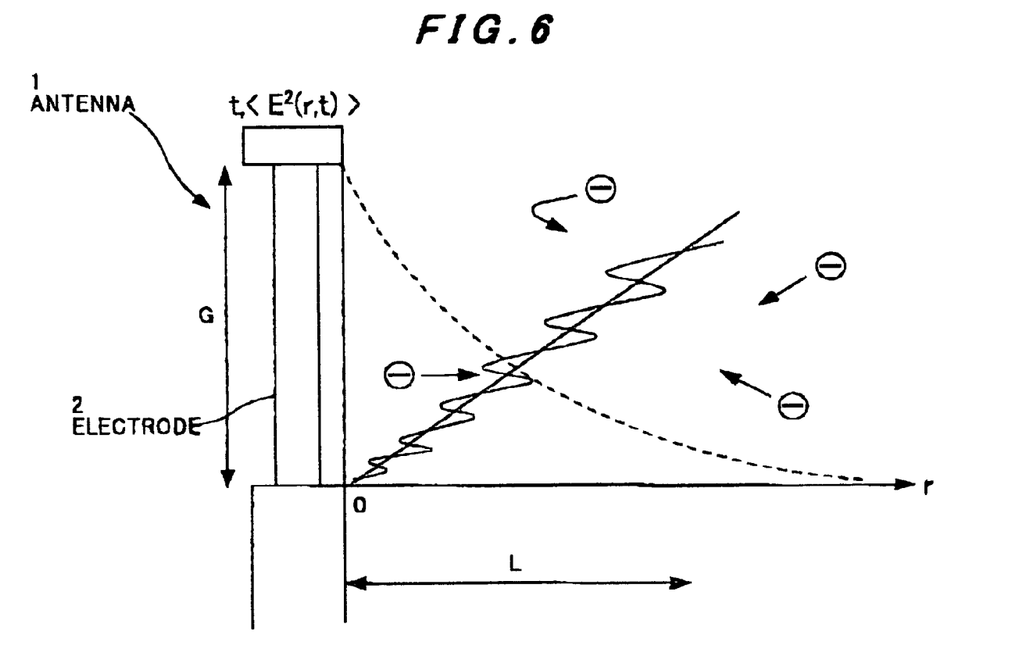
FIG. 6 is an explanatory diagram illustrating a state that electrons are repelled by the dynamic gravity effect from the vicinity of electrode 2 in FIG. 5.

FIG. 6 illustrates integrally the antenna 1 and electrode 2 with the gap 25 (G) exaggerated, the visualization of electric field formed, the intensity graph (dotted curve) of electric field to distance, and the behavior (solid curve) of electrons. When radio-frequency power is supplied to the antenna 1, electric field E is generated. The electric field E is a local radio-frequency electric field E(r,t) that is a function of a radial distance r and a time t. The dynamic gravity (repulsive force) f acting on electron located at a distance r and the dynamic gravity potential $\phi$ are represented by:

$$f = e\frac{d\varphi}{dr}$$
$$= -(e^2/2m\omega^2)(d<E^2(r, t)>/dr) \text{ and}$$
$$\varphi = -\frac{e<E^2(r, t)>}{2m\omega^2}$$

respectively where e is charge of electron, m is electron rest mass and $\omega$ is angular frequency. $<E^2(r,t)>$ is time-averaged electric field.

Then, the conditions for generating the dynamic gravity are represented by:

$$\omega >> 2\upsilon/L$$

$$(\frac{1}{2})\epsilon_0 <E^2(r,t)>>>nT$$

where $\upsilon$ is thermal velocity of electron, L is characteristic length, $\epsilon_0$ is dielectric constant in vacuum, n is electron density and T is electron temperature.

Meanwhile, characteristic length L is defined as a distance until when initial electric field $E_0$ is reduced to $E_0/2.718$.

$$E=E_0 e^{-r/L}$$

If the abovementioned conditions are satisfied, an electron to move away from the antenna 1 can get away therefrom and however, an electron to come close to the antenna 1 cannot get close thereto because it is repelled by the dynamic gravity from the radio-frequency electric field E. Thus, the radio-frequency electric field E defines a wall that repels the electron. This phenomenon is called dynamic gravity effect.

On the other hand, since ion particle (in plasma) is not subjected to a strong repulsive force even under the above-mentioned conditions, it can easily pass through the wall and reach the antenna 1. Thus, the ion particle collides with the electrode 2 provided on the antenna 1 and current is thereby flown through the electrode 2.

Figure 8:
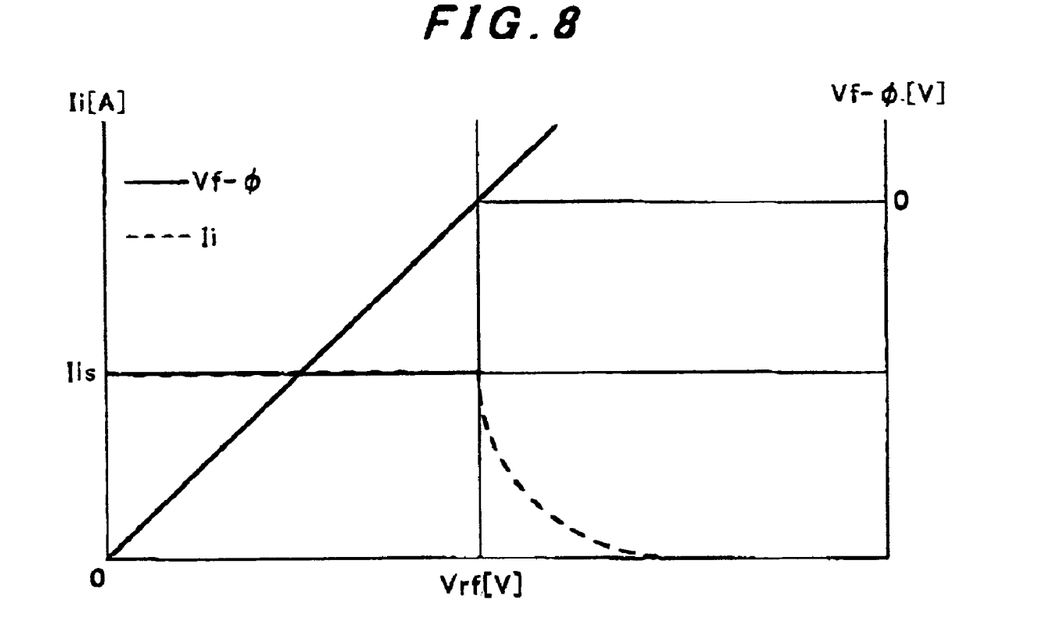
FIG. 8 is an explanatory diagram illustrating the process of determining a plasma potential according to the invention.

If the potential of electrode 2 is lower than the plasma potential, many ion particles collide with the electrode 2 and the ion current flows ($I_{is}$ in FIG. 8). As the potential of electrode 2 comes close to the plasma potential from a level lower than the plasma potential and then exceeds the plasma potential, the number of ion particles to collide with the electrode 2 decreases and the current flow decreases ($I_i < I_{is}$ in FIG. 8).

Thus, in the plasma potential measuring apparatus as shown in FIG. 1, when radio-frequency electric field E is applied from the antenna 1 to the plasma atmosphere P, a wall is formed that only the ion particle selectively can pass through from the plasma atmosphere P and the low energy electron cannot pass through. A space surrounded by the wall is the measurement space A as shown in FIG. 5.

In the measurement space A, the floating potential of electrode 2 at the time when the ion current to the internal electrode 2a begins to decrease can be regarded as the plasma potential. In the case that the radio-frequency electric field E is not applied, when an object is put in the plasma atmosphere P, a floating potential is generated at the boundary between the object and the plasma atmosphere P. Therefore, the plasma potential can be obtained by adding a sheath voltage to the floating potential of electrode 2.

The dynamic gravity effect is conventionally known. For example, the dynamic gravity effect is used such that a dynamic gravity field conditioned to repel ion particles is formed on the entire inner wall of plasma chamber to control the flow of ion particles to the inner wall. However, the technique of the invention is not known that the plasma potential is measured by employing the ponderomotive effect acted only on electrons.

Figure 7:
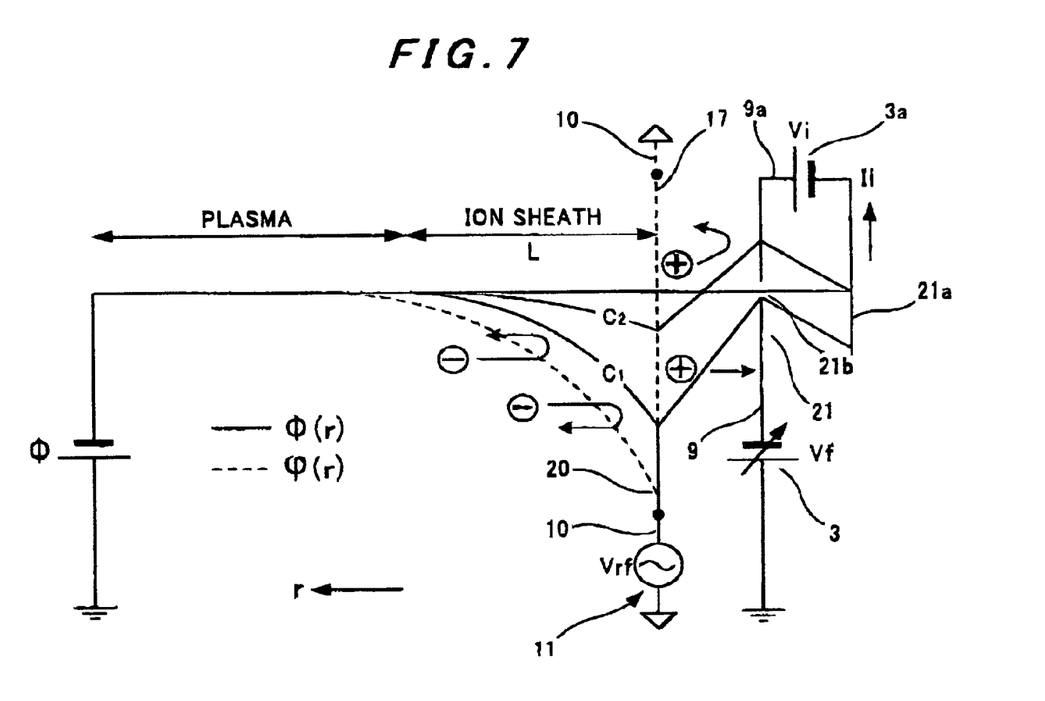
FIG. 7 is an explanatory diagram illustrating a model defined in the plasma potential measuring method of the invention.

FIG. 7 is an explanatory diagram illustrating a model defined in the plasma potential measuring method of the invention. In FIG. 7, the plasma potential $\phi$, the radio-frequency voltage $V_{rf}$ applied to the antenna 1, and the floating potential $V_f$ of electrode 2 behind the antenna 1 each are illustrated as a power source image. The image of potential barrier to repel electrons and to allow ions to pass through is indicated by dotted curve. The barrier is estimated to be close to the electrode 2 as much as possible. The lateral direction represents a distance r from the antenna 1.

It is assumed that, in the vicinity of the antenna 1, a sheath is formed by electric field from plasma potential $\phi$ to the antenna 1. In FIG. 7, solid line or curve represents a spacial distribution $\phi$ (r) in plasma potential located all over from plasma section to ion sheath section, and dotted curve represents a spacial distribution $\phi$ (r) in dynamic gravity potential $\phi$ acting only on electron located all over the same section. A place sufficiently distant from the antenna 1 is a plasma region with a constant plasma potential $\phi$. As the radio-frequency voltage $V_{rf}$ applied to the antenna 1 is increased, electrons are repelled by the dynamic gravity and the potential of ion sheath section begins to rise in $\phi$ (r) distribution represented by the solid curve ($C_1$). When the radio-frequency voltage $V_{rf}$ is further increased, the potential of electrode 2 increases exceeding $\phi$ and even the ion particle is repelled ($C_2$).

FIG. 8 is an explanatory diagram illustrating the process of determining a plasma potential according to the invention, where the plasma potential is effectively determined from the detection result of current $I_i$.

In FIG. 8, a vertical coordinate axis on the left side represents current $I_i$ to flow into the internal electrode 2a, a vertical coordinate axis on the right side represents potential difference ($V_f$-ϕ) between the floating potential $V_f$ on the electrode 2 and the plasma potential ϕ, and a lateral coordinate axis represents radio-frequency voltage $V_{rf}$. A plotted solid line indicates the change of potential difference ($V_f$-ϕ) along with the change of radio-frequency voltage $V_{rf}$. A dotted line and curve indicates the change of current $I_i$ along with the change of radio-frequency voltage $V_{rf}$.

In the plasma potential measuring apparatus and method, the probe 8 of the above embodiment has the next effects.

(1) Since the cylinder 17 and cap member 19 have a cylindrical structure with the same diameter, the radio-frequency electric field E is in axial symmetry (in rotational symmetry) generated all around the antenna 1. Therefore, the barrier to electron can be formed uniform to prevent the leakage of electron. Thereby, the ion current can be accurately measured.

(2) Since the antenna 1 is composed of the gap 25, the intensity (amplitude) of radio-frequency electric field E can be increased by adjusting the length G (See FIG. 6) of gap 25. Namely, if electric power is constantly supplied from the radio-frequency source 11, the potential gradient is made steep by narrowing the length G and thereby the intensity radio-frequency electric field E can be increased. For convenience of illustration, the length G of gap 25 between the cylinder 17 and the cap member 19 is shown greater than real one and, however, it should be exactly about 1 mm or less. Further, it may be reduced to the extent that particle can pass through. By thus reducing the length G, the intensity of radio-frequency electric field E can be increased. Therefore, the electric power supplied to the radio-frequency source 11 can be reduced by that much. Thereby, the entire probe 8 can be downsized.

(3) Since the electrode 2 is composed of the copper tuber 21 and the internal conductor 23 disposed at the axial center of the electrode 2 is electrically connected to the cap member 19, the radio-frequency power can be supplied from the base end of probe 8 to the cap member 19.

Although in the above embodiment the antenna 1 is composed of the gap 25 between the cylinder 17 and cap member 19, the structure of antenna 1 is not limited that composition. The antenna 1 may have any shapes if it can generate radio-frequency electric field E to repel electrons that come close to the electrode 2. Although the wall defined by the radio-frequency electric field E varies depending on the shape of antenna 1, the invention can be executed as long as the measurement space A surrounded by the radio-frequency electric field E is formed.

Although in the above embodiment the electrode 2 and the internal electrode 2a each are composed of the copper tube 21 and the inner cylinder 21a, they are not limited to that composition. If they can be accommodated in the measurement space A surrounded by the radio-frequency electric field E, the electrode 2 and the internal electrode 2a each may have any shapes.

Although the invention has been described with respect to the specific embodiments for complete and clear disclosure, the appended claims are not to be thus limited but are to be construed as embodying all modifications and alternative constructions that may occur to one skilled in the art which fairly fall within the basic teaching herein set forth.

What is claimed is:

1. A plasma potential measuring method, comprising:
   providing a measurement space surrounded by a radio-frequency electric field in a plasma atmosphere;
   monitoring a floating potential at an electrode located in the measurement space in a process of increasing the radio-frequency electric field; and
   detecting a value of the floating potential at the time when an ion current flowing into the electrode begins to lower; and
   determining a plasma potential in said plasma atmosphere based on said detected value of the floating potential.

2. The plasma potential measuring method according to claim 1, wherein said providing the measurement space is conducted such that the measurement space is formed in the plasma atmosphere using a dynamic gravity effect to repel electrons that come close to the electrode.

3. The plasma potential measuring method according to claim 2, wherein said dynamic gravity effect comprises a ponderomotive effect.

4. The plasma potential measuring method according to claim 1, wherein said monitoring comprises varying the floating potential of the electrode from a value lower than the plasma potential to a value greater than the plasma potential.

5. The plasma potential measuring method according to claim 1, wherein the measurement space is locally provided in the plasma atmosphere.

6. A plasma potential measuring apparatus, comprising:
   an antenna that forms a measurement space surrounded by a radio-frequency electric field in a plasma atmosphere;
   a radio-frequency source for supplying a radio-frequency power;
   an electrode that is located in the measurement space;
   an internal electrode that captures a part of ions that flows into the electrode;
   an ion current determination section that determines a reduction in an ion current that flows into the electrode in a process of increasing the radio-frequency electric field; and
   a potential determination section that determines as a plasma potential a floating potential of the electrode at the lime when the ion current begins to decrease.

7. The plasma potential measuring apparatus according to claim 6, wherein the measurement space is formed in the plasma atmosphere using a dynamic gravity effect to repel electrons that come close to the electrode, the dynamic gravity effect being provided by the radio-frequency electric field generated in the vicinity of the antenna.

8. The plasma potential measuring apparatus according to claim 6, wherein the internal electrode is located within the electrode.

9. The plasma potential measuring apparatus according to claim 6, wherein the antenna comprises a plurality of electrodes, a gap being formed between the electrodes.

10. The plasma potential measuring apparatus according to claim 9, wherein an amplitude of the radio-frequency electric field is adjustable by adjusting a length of the gap.

11. A plasma potential measuring probe, comprising:
    a radio-frequency source for supplying a radio-frequency power;
    a rod-shaped electrode that is used to apply the radio-frequency power;
    an opposite electrode that is used to apply radio-frequency power and is disposed by a gap distant from a front end of the rod-shaped electrode;

a floating potential detecting electrode that is disposed in a radio-frequency electric field fanned by the radio-frequency power supplied to the rod-shaped electrode and the opposite electrode; and an ion current detecting electrode tat is disposed in a vicinity of the floating potential detecting electrode so as to capture part of ions which flow into the floating potential detecting electrode in a process of increasing the radio-frequency electric field.

12. The plasma potential measuring probe according to claim 11, wherein the floating potential detecting electrode and the ion current detecting electrode comprise coaxial conductive tubes, and wherein the opposite electrode is provided with a feeder line passing through the coaxial conductive tubes.

13. The plasma potential measuring probe according to claim 11, wherein an amplitude of the radio-frequency electric field is adjustable by adjusting a length of the gap.

14. The plasma potential measuring probe according to claim 11, wherein said rod-shaped electrode and said opposite electrode comprise cylindrical electrodes having a same diameter, such that said radio-frequency electric field comprises an axially symmetrical electric field formed around said gap.

15. The plasma potential measuring probe according to claim 11, wherein said floating potential detecting electrode comprises a copper tube, and said ion current detecting electrode comprises a cylinder fanned in said copper tube.

16. A plasma potential measuring apparatus, comprising:
a pair of electrodes which are separated by a gap and apply radio-frequency power, such That a radio-frequency electric field is formed in a plasma atmosphere in an area of said gap;

a floating potential detecting electrode which is connected to a power source and disposed in a measuring space in said plasma atmosphere, for detecting a floating potential; and an ion current detecting electrode that is disposed in a vicinity of the floating potential detecting electrode, for detecting an ion current for ions flowing across said floating potential detecting electrode, wherein a plasma potential is given as said floating potential detected at a time when said ion current begins to decrease in a process of increasing the radio-frequency electric field.

17. The plasma potential measuring apparatus according to claim 16, wherein said process of increasing the radio-frequency electric field comprises gradually adjusting a potential applied from said power source from a low value to a high value.

18. The plasma potential measuring apparatus according to claim 16, wherein said floating potential detecting electrode is connected to a potential determination section which detects a potential applied to said floating potential detecting electrode and a current flowing from said power source to said floating potential detecting electrode.

19. The plasma potential measuring apparatus according to claim 18, wherein said floating potential comprises a value of said applied potential detected at a time when a flow of said current is stopped.

20. A plasma potential measuring method, comprising:
forming a radio-frequency electric field in a plasma atmosphere in an area of a gap which separates a pair of electrodes which apply radio-frequency power;

detecting a floating potential using a floating potential detecting electrode which is connected to a power source and disposed in a measurement space in said plasma atmosphere;

detecting an ion current for ions flowing across said floating potential detecting electrode using an ion current detecting electrode that is disposed in a vicinity of the floating potential detecting electrode; and determining a plasma potential in said plasma atmosphere by using said detected floating potential, wherein said plasma potential is given as said floating potential detected at a time when said ion current begins to decrease in a process of increasing the radio-frequency electric field.

* * * * *